(12) United States Patent
Valkonen et al.

(10) Patent No.: US 6,873,353 B1
(45) Date of Patent: Mar. 29, 2005

(54) METHOD FOR SYNCHRONIZING IMAGE DATA OBTAINED FROM PROCESS MONITORING CAMERAS

(75) Inventors: Mika Valkonen, Äänekoski (FI); Juha Toivonen, Jyväskylä (FI); Jorma Snellman, Säynätsalo (FI)

(73) Assignee: Honeywell Oy (FI)

( * ) Notice: Subject to any disclaimer, the term of this patent is extended or adjusted under 35 U.S.C. 154(b) by 0 days.

(21) Appl. No.: 09/515,537

(22) Filed: Feb. 29, 2000

(30) Foreign Application Priority Data

Mar. 1, 1999 (FI) ................................................ 990428

(51) Int. Cl.⁷ ................................................ H04N 7/18
(52) U.S. Cl. ........................... 348/88; 348/61; 348/86; 348/159
(58) Field of Search ........................... 348/88, 86, 61, 348/159, 154, 163, 475

(56) References Cited

U.S. PATENT DOCUMENTS

| | | | | |
|---|---|---|---|---|
| 4,922,337 A | * | 5/1990 | Hunt et al. ................... | 348/88 |
| 4,992,866 A | * | 2/1991 | Morgan ....................... | 348/159 |
| 5,239,376 A | | 8/1993 | Dittmann et al. ............ | 358/101 |
| 5,717,456 A | * | 2/1998 | Rudt et al. ................... | 348/88 |
| 5,767,980 A | * | 6/1998 | Wang et al. ................. | 358/475 |
| 5,956,081 A | * | 9/1999 | Katz et al. ................... | 348/163 |
| 5,995,140 A | * | 11/1999 | Cooper et al. .............. | 348/159 |
| 6,359,647 B1 | * | 3/2002 | Sengupta et al. ........... | 348/154 |

FOREIGN PATENT DOCUMENTS

| | | | |
|---|---|---|---|
| EP | 0 366 235 A1 | 5/1990 | |
| EP | 0837323 | 4/1998 | |
| EP | 0 837 323 A2 * | 4/1998 | .......... G01N/21/89 |
| EP | 0 847 201 A1 | 6/1998 | |
| FI | 973611 | 11/1997 | |

* cited by examiner

Primary Examiner—Allen Wong
(74) Attorney, Agent, or Firm—Ostrolenk, Faber, Gerb & Soffen, LLP

(57) ABSTRACT

The object of the invention is a method for synchronizing image data obtained from process monitoring cameras. By utilizing synchronization, one and the same area in a paper web can be sought as it passed the different camera positions. Since the speed are high and the webs somewhat stretching, synchronization does not often directly result in the same area being shown in the different camera positions. To facilitate search, a selection area corresponding to the limited number of sequential images in the environment of the point of synchronization of each camera position is visualized for the operator, inside which area the corresponding area in the web can be found with certainty.

20 Claims, 2 Drawing Sheets

METHOD FOR SYNCHRONIZING IMAGE DATA OBTAINED FROM PROCESS MONITORING CAMERAS

FIELD OF THE INVENTION

The present invention relates generally to synchronizing image data, and, more particularly, selecting related images from a plurality of different camera positions.

BACKGROUND OF THE INVENTION

When an operator of several cameras films an event, for example, to analyze a paper web, and finds an interesting object, by utilizing synchronization, he will be able to see the same area in the paper web as it passes other camera positions. This type of synchronization has long been a characteristic of the Applicant's operations. However, its use involves certain problems or deficiencies. Due to the high speed and stretching of the web, it is not possible for synchronization to be so accurate as to necessarily show the corresponding area in the web in the new position shown by the synchronization. If there is, for example, an interruption at the dry end of the machine and the operator of the monitoring system searches for the same area in the web at the wet end of the machine, the operator cannot be absolutely certain whether the object is located in the area of the video recording displayed as a result of synchronization, in which case the operator is likely to discontinue the search.

SUMMARY OF THE INVENTION

The present invention is provided for improved synchronizing of image data obtained from process monitoring cameras, wherein different positions in the process are imaged using various cameras;

image data from the different camera positions is stored per camera into digital image processors;

images stored at the different camera positions are selected for display and analysis on the operator's computer screen; and from the image data obtained at the different camera positions are searched images depicting the same area in the web by using synchronization means.

BRIEF DESCRIPTION OF THE DRAWINGS

An exemplary embodiment of the invention is described in the following with reference to the accompany drawings in which.

DETAILED DESCRIPTION OF THE PREFERRED EMBODIMENT

The aim of the present invention is to provide an improved synchronization method, so that the operator will know for certain that he will arrive automatically in the middle of the visualized area, inside which the desired same area of the web can be found. The idea is, therefore, to compel the operator to go through an area of sequential images of a size that can be parameterized. In such a case, the corresponding area in the web in different camera positions will be found more reliably and easily.

The general structure and operation of the system are first described before disclosing the manner according to the invention for visualizing the area of sequential images to be synchronized to the operator.

Figure 1:
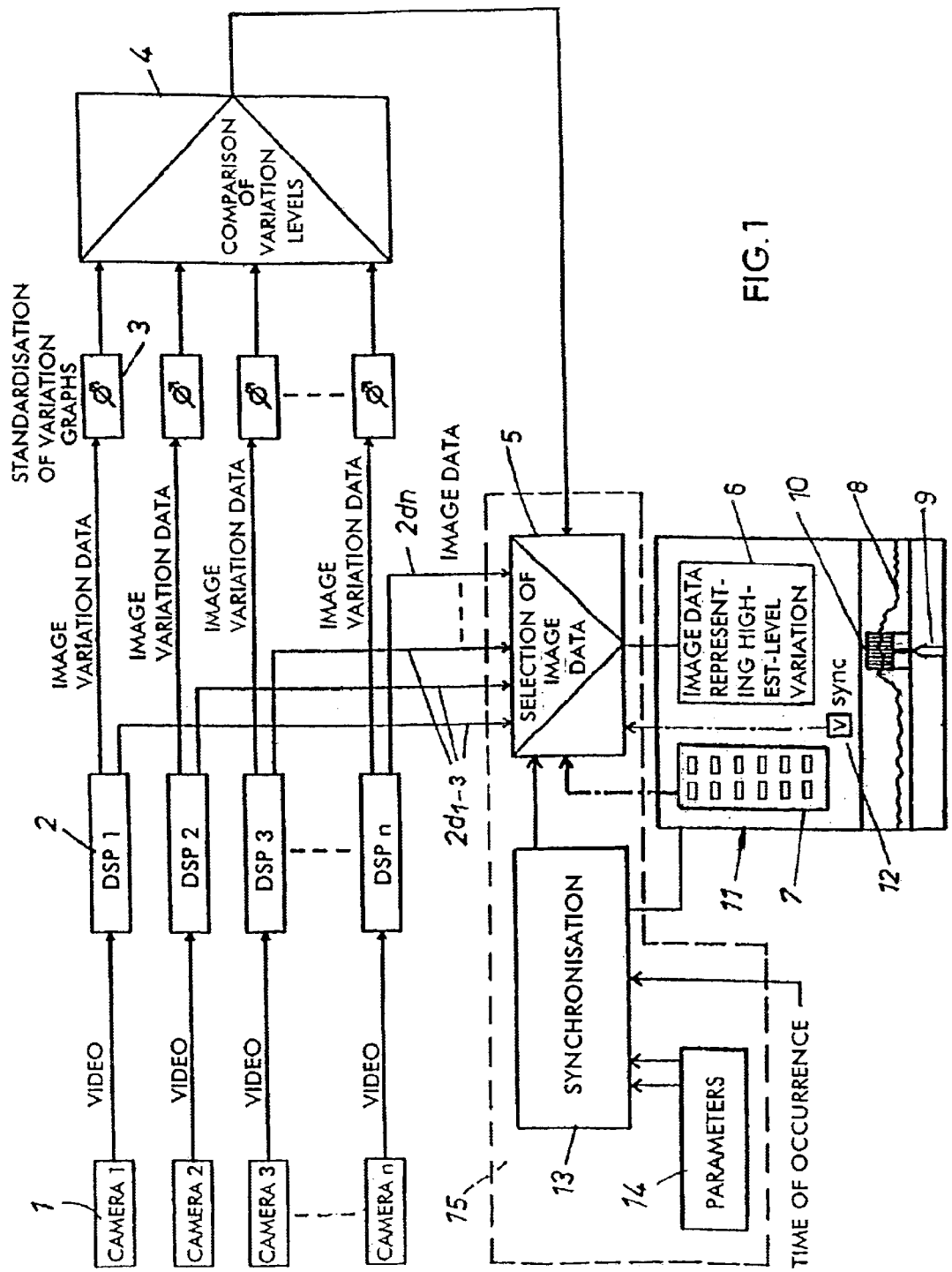
FIG. 1 shows the system used for implementing the synchronization method relating to the invention as a flow chart.

In the flow chart shown in FIG. 1, the image source is a video camera 1 which produces a continuous video image of the object being monitored. The image data is processed in a digital signal processor 2, or DSP processor. Signal processors are similar to ordinary microprocessors, but contain, among others, the use of floating-point number technology and address formats for easier addressing. Furthermore, the DSP is markedly different from the ordinary processor in terms of its architecture, having been designed for duties involving large amounts of data, and where multiplication with integers and data transfers are statistically significant operations. DSP processors are capable of performing a plurality of different and simultaneous calculation routines associated with image analysis, the results of which can be applied automatically to monitoring changes in image data.

The system comprises several video cameras 1 for imaging the various positions of the process being monitored. Each camera is provided with its own digital image processor 2 for storing digital image data per camera. The signal processors 2 are used for analyzing each camera-specific image data item so as to provide image variation data based on the level of variation in a plurality of sequential images. From the signal processors 2 the said image data and image variation data are transmitted to an analyzing computer 15 which has a display 11.

The images stored at the different camera positions can be selected for analysis by means of selector icons 7. The image variation graph 8 corresponding to the image variation data of images preceding and following the image to be analyzed is displayed at the bottom of the screen 11. A floating arrow designated by reference numeral 9 indicates the point on the image variation graph 8 at which the image 6 displayed is located. The floating arrow 9 can be used for selecting an image at any point on the graph 8 for display. The image data $2d_1-2d_n$ stored from each camera position 1–n may encompass several hundred images. Depending on the process, the image data in store at each time may have a duration ranging from a few seconds to several minutes, and the storage may function on the FIFO (first in first out) principle.

Since each image variation graph 8 shown at the bottom of the screen 11 is prepared of image material from each respective camera position, the image variation graphs of the different camera positions can be standardized so as to be comparable, and be compared with each other, whereby the image variation graph representing the highest-level variation and the image data of the camera position corresponding to it can be selected automatically for displaying on the analyzing window of the screen 11. For the purpose of this automation, the system is provided with standardizing means 3 for standardizing the output levels of the image variation data of the different camera positions to be mutually comparable. A comparison between the standardized image variation levels of the different camera positions is performed by means of comparator means 4. Selector means 5 receive image data from the different camera positions and select, under the control of the comparator means 4, the image data $2d_1-2d_n$ representing the highest-level variation and the corresponding image variation graph 8 to be displayed on the screen 11. Image 6 is one of a multitude of images included in the image data. The graph 8 and the floating indicator 9 can be used for examining those very images 6 associated with the area of the highest-level image variation. The image 6 on the screen 11 may represent, for example, a hole formed in a paper web.

The automated selection of the image 6, as described above, is obviously optional, meaning that the operator may, if he so desires, select image data $2d_1$–$2d_n$ from any camera position for analysis. However, it is often useful for the operator to know at the very beginning of analysis which camera position produced the highest-level image variation, in which case the analysis can be started from this particular camera position.

The operator's data processing means 15 comprise synchronization means 12, 13, 14 by means of which images depicting the same area in the web can be sought automatically from the image data of different camera positions. When the synchronization option 12 is displayed on the screen 11, the synchronization unit 13 controls the image data selection unit 5 in such a way that the selection of a camera position by means of the selector icons 7 automatically produces on the screen 11 the image 6 which corresponds to the same area in the paper web as the image 6 of the previous camera position. For this purpose the synchronization unit 13 requires certain parameters 14, which include at least web speed and the distances between the cameras 1. The synchronization unit 13 is also given a time of occurrence 2t at which an interesting object was observed in the image field of a camera position, the web area corresponding to which having to be analyzed from the different camera positions.

Figure 2:
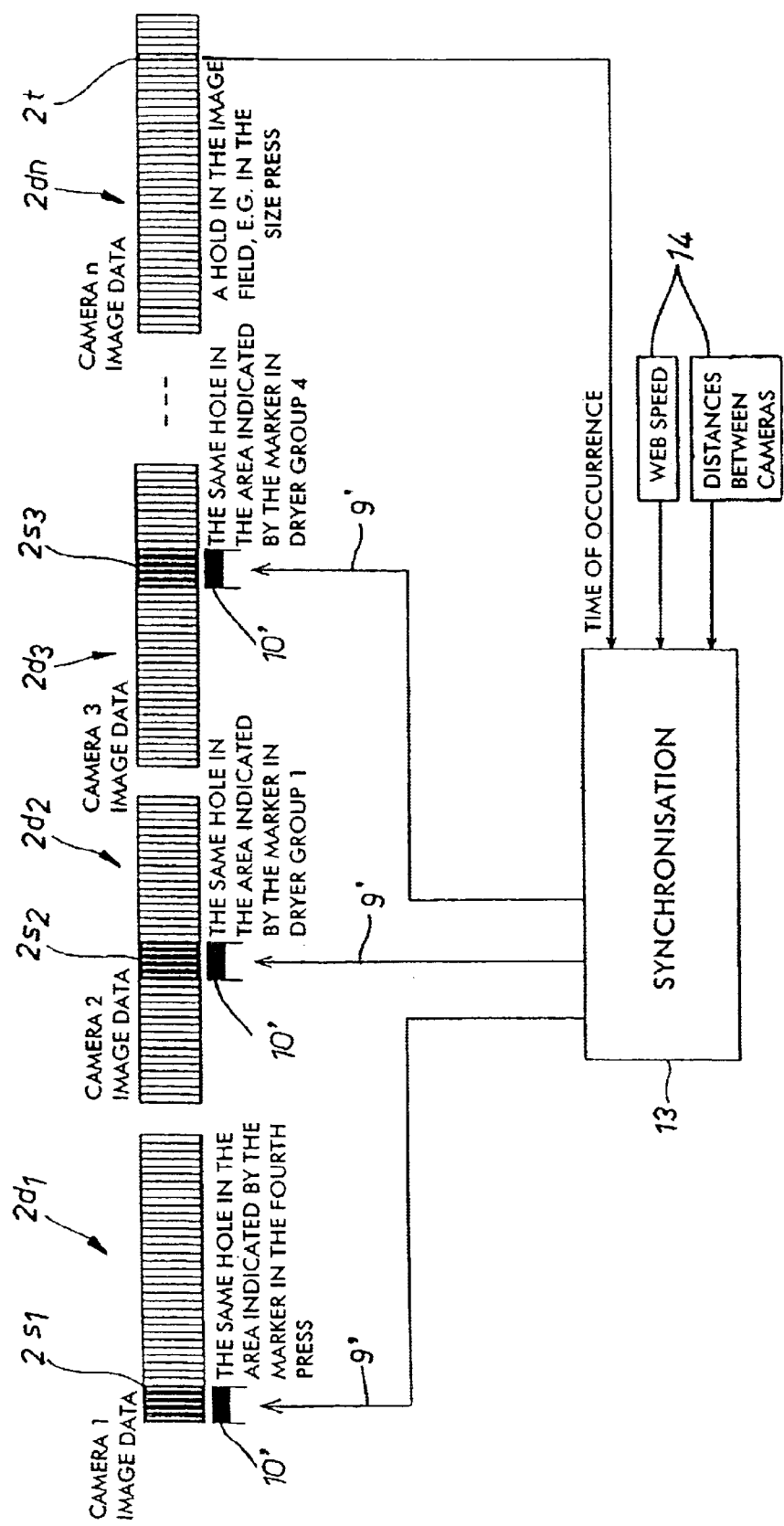
FIG. 2 illustrates the performance of synchronization on the basis of image data from different camera positions.

FIG. 2 shows a hole, for example to the size press, to an image produced at point of time 2t in the image data $2d_n$ of camera n. On the basis of the time of occurrence and other parameter data, the synchronization unit 13 is able to determine, by means of simple calculations, the images $2s_1$–$2s_3$ in the image data $2d_1$–$2d_3$ in which the same hole appears. The accuracy of synchronization cannot, however, be very high due to the high speed and stretching of the web, and thus in the invention is specified a selection area 10, 10' of a certain width, which is visualized for the operator, within which the corresponding point in the web will be found with certainty. For the operator is thus visualized a section selection area 10 in the environment of the point of synchronization 9, 9' of each camera position, within which area there is a limited number of sequential images among which the corresponding point will be found with certainty. The said limited number is preferably a minimum number determined by the parameters such as web speed and distance between the camera positions. This marker selection area 10 motivates the operator to search for the corresponding point in the different camera positions. The size of the selection area 10, that is, the number of images contained by it is, therefore, dependent on web speed and the distances between the cameras.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method for displaying a plurality of images of a moving object obtained from a plurality of cameras, the method comprising:

placing each of the plurality of cameras is a position to take a respective image different from the images taken by the other cameras;

taking images using at least some of the cameras;

storing image data from the images in digital image processors;

obtaining variation information from the image data, the variation information representing a variation in a sequence of images from at least two of the cameras;

comparing the variation information from each of the two cameras to determine a first camera that provided the highest degree of variation in the sequence of images;

displaying a single image of the object from the sequence of images received from the first camera;

synchronizing the image information representing images received from, at least two other cameras to illustrate the object shown in the single image;

defining a first parameter representing distance between at least two of the plurality of cameras and a second parameter representing velocity of the moving object; and providing a user interface comprising a selection area that uses the first and second parameters to represent fewer than all images in the sequence of images from one of the plurality of cameras, the interface further comprising a selection control to select an image in the sequence of images, wherein the number of images represented by the selection area depends on the speed of the moving object and the distance between at least two of the cameras, and wherein images from the at least two cameras are displayed that correspond to the image selected by the selection control.

2. A method for representing synchronized image data from images of a moving web obtained from a plurality of cameras, the method comprising:

placing each of the plurality of cameras is positions to take respective images different from the images taken by the others of the plurality of cameras;

obtaining a set of images using at least some of the cameras;

defining a first parameter representing distance between at least two of the cameras and a second parameter representing the velocity of the web;

storing image data from the set of images in at least one digital image processor;

selecting at least some images from the set of images showing a selected area of the web obtained from a first camera for display on a computer screen;

searching the image data according to synchronization rules that utilize the first parameter and the second parameter to select images obtained from a second camera which show the selected area of the web; and displaying a selection area on the computes screen that represents images that correspond to the image data from the selected images.

3. The method of claim 2, wherein the web is in a paper manufacturing machine, and further comprising monitoring the web in the paper manufacturing machine.

4. The method of claim 3, further comprising analyzing and compiling image variation data based on a level of variation in sequential images obtained from at least one of the cameras, and displaying an image variation graph corresponding to the image variation data.

5. The method of claim 4, further comprising, standardizing the output levels of the image variation data of the images obtained from the different cameras so as to be mutually comparable, comparing the standardized output levels of the image variation data, and selecting the image data for a respective camera representing the highest-level variation for automatic display.

6. The method of claim 3, further comprising analyzing and compiling image variation data based on a level of variation in a plurality of sequential images obtained from at least some of the cameras, standardizing the output levels of the image variation data of the images taken by the different cameras so as to be mutually comparable, comparing the standardized output levels of the image variation data, and selecting the image data for a respective camera representing the highest level variation for automatic display.

7. The method of claim 2, further comprising analyzing and compiling image variation data based on a level of variation in the fewer than all images, and displaying an image variation graph corresponding to the image variation data.

8. The method of claim 7, further comprising standardizing the output levels of the image variation data of the images obtained from the different cameras so as to be mutually comparable, comparing the standardized output levels of the image variation data, and selecting the image data for a respective camera representing the highest-level variation for automatic display.

9. The method of claim 2, further comprising analyzing and compiling image variation data based on a level of variation in a plurality of sequential images taken obtained from at least some of the cameras, standardizing the output levels of the image variation data from the images obtained from the different cameras so as to be mutually comparable, comparing the standardized output levels of the image variation data, and selecting the image data for a respective camera representing the highest-level variation for automatic display.

10. The method of claim 2, wherein the selection area includes a pointer, the pointer enabling the operator to select at least one of the images.

11. A method for representing synchronized image data from images of a moving paper web obtained from a plurality of cameras, the method comprising:
   placing each of the plurality of cameras in positions to take respective images different from the images taken by the others of the plurality of cameras;
   obtaining a set of images using at least some of the cameras;
   defining a first parameter that represents the distance between at least two of the cameras, and a second parameter that represents the velocity of the paper web;
   storing image data from the set of images in at least one digital image processor;
   selecting at least some images from the set of images that correspond to respective image data from of images of a selected area of the web obtained from a first one of the cameras;
   searching the image data according to synchronization rules that utilize the first and second parameters to locate images taken from at least a second of the cameras which show the selected area in the paper web; and
   displaying a selection area on the operator's computer screen representing fewer than all images from one of the cameras, wherein the selection area represents a first synchronized image that originates from one camera and changes to a second synchronized image originating from another camera.

12. The method of claim 11, wherein the paper web is in a paper manufacturing machine, and further comprising monitoring the paper web in the paper manufacturing machine.

13. The method of claim 12, further comprising analyzing and compiling image variation data based on a level of variation in sequential images obtained from at least one of the cameras, and displaying an image variation graph corresponding to the image variation data.

14. The method of claim 13, further comprising, standardizing the output levels of the image variation data of the images obtained from the different cameras so as to be mutually comparable, comparing the standardized output levels of the image variation data, and selecting the image data for a respective camera representing the highest-level variation for automatic display.

15. The method of claim 12, further comprising analyzing and compiling image variation data based on a level of variation in a plurality of sequential images obtained from at least some of the cameras, standardizing the output levels of the image variation data of the images taken by the different cameras so as to be mutually comparable, comparing the standardized output levels of the image variation data, and selecting the image data for a respective camera representing the highest-level variation for automatic display.

16. The method of claim 11, further comprising analyzing and compiling image variation data based on a level of variation in a plurality of sequential images obtained from at least some of the cameras and displaying an image variation graph corresponding to the image variation data of at least one image preceding and following an image to be analyzed.

17. The method of claim 16, further comprising, standardizing the output levels of the images variation data of the images obtained from the different cameras so as to be mutually comparable, comparing the standardized output levels of the image variation data, and selecting the image data for a respective camera representing the highest-level variation for automatic display.

18. The method of claim 11, further comprising analyzing and compiling image variation data based on a level of variation in a plurality of sequential images obtained from at least some of the cameras, standardizing the output levels of the image variation data of images taken by the different cameras so as to be mutually comparable, comparing the standardized output levels of the image variation data, and selecting the image data for a respective camera representing the highest-level variation for automatic display.

19. The method of claim 11, wherein the selection area includes a pointer, the pointer enabling the operator to select at least one of the images.

20. A method, for monitoring a web process comprising the steps of placing a plurality of cameras at different process locations with different fields of view:
   creating image streams using at least some of the cameras;
   storing image data from the image streams in at least one digital image processor;
   defining a first parameter representing distance between at least two of the plurality of cameras and a second parameter representing at least velocity of the web;
   selecting an area of interest at a particular position along the web; and
   tracking the selected area as the web moves through the process by:
      selecting at least some images for display on a computer screen which show the selected area as viewed by a first camera;
      searching the image data according to synchronization rules that utilize the first and second parameters to locate images depicting the selected area as viewed by a second camera; and
      displaying a selection area on the computer screen that represents images of the selected area as viewed by the first and second cameras.

* * * * *